United States Patent [19]
Devauchelle et al.

[11] Patent Number: 5,597,689
[45] Date of Patent: Jan. 28, 1997

[54] NUCLEOTIDE SEQUENCES PERMITTING THE REPLICATION AND MAINTENANCE OF A GENETIC INFORMATION IN ANIMAL CELLS

[75] Inventors: Gérard Devauchelle; Martine Cerutti, both of Saint Christol-Les-Ales; Cécile Persillon, Alles, all of France

[73] Assignees: Institut National de la Recherche Agronomique (I.N.R.A.); Centre National de la Recherche Scientifique (C.N.R.S.), both of Paris, France

[21] Appl. No.: 280,320

[22] Filed: Jul. 26, 1994

[30] Foreign Application Priority Data

Jul. 26, 1993 [FR] France .................... 93 09156

[51] Int. Cl.$^6$ .............................. C12Q 1/70; C12N 15/64
[52] U.S. Cl. .................. 435/5; 435/6; 435/91.41; 435/172.3; 435/320.1; 435/348; 536/23.72; 536/24.1
[58] Field of Search ................. 435/69.1, 172.1, 435/172.3, 240.2, 320.1, 5, 6, 91.41; 536/23.1, 23.72, 24.1

[56] References Cited

U.S. PATENT DOCUMENTS 5,004,687  4/1991  Miller .................... 435/69.1

FOREIGN PATENT DOCUMENTS 0536646  4/1993  European Pat. Off. .

OTHER PUBLICATIONS

Pennoch et al., "Strong and Regulated Expression of *Escherichia coli* β-Galactosides in Insect Cells with a Baculovirus Vector", Mol. Cell. Biol., vol. 4, No. 3, Mar. 1984, pp. 399–406.

Hooft, B. J. L. et al., "Detection of Sequences in Autographa californica Nuclear Polyhedrosis Virus DNA, that Act as Autonomous Replicating Sequences (ARS) in Yeast," Archives of Virology, vol. 88, 1986, pp. 279–284.

Guarino, L. A. and Summers, M. D., "Nucleotide Sequence and Temporal Expression of a Baculovirus Regulatory Gene," Journal of Virology, vol. 61, No. 7, Jul. 1987, pp. 2091–2099.

Lee, H. Y. et al., "Identification of bent DNA and ARS fragments in the genome of *Choristoneura fumiferana* nuclear polyhedrosis virus," Virus Research, vol. 24, 1992, pp. 249–264.

Leisy, D. and Rohrmann, G. F., "Characterization of the Replication of Plasmids Containing hr Sequences in Baculovirus-Infected *Spodoptera frugiperda* Cells," Virology, vol. 196, No. 2, Oct. 1993, pp. 772–730.

*Primary Examiner*—David Guzo
*Attorney, Agent, or Firm*—Bell, Seltzer, Park & Gibson

[57] ABSTRACT

The subject of the invention is the use of a DNA fragment comprising a sequence from the 3' end of the AcNPV baculovirus IE1 gene, optionally combined with a DNA fragment comprising a sequence situated upstream of the promoter of the IE1 gene, for producing vectors permitting the replication and maintenance of genetic information in animal cells.

The invention also encompasses the episomal vectors obtained, as well as the transformed cells comprising the vectors.

8 Claims, 15 Drawing Sheets

FIGURE 2 A : pIE1
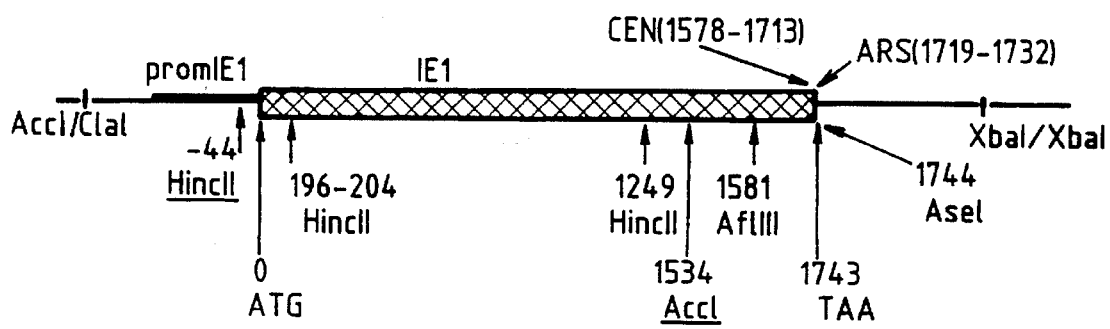
FIGURE 2 B : pIE1 NeoR
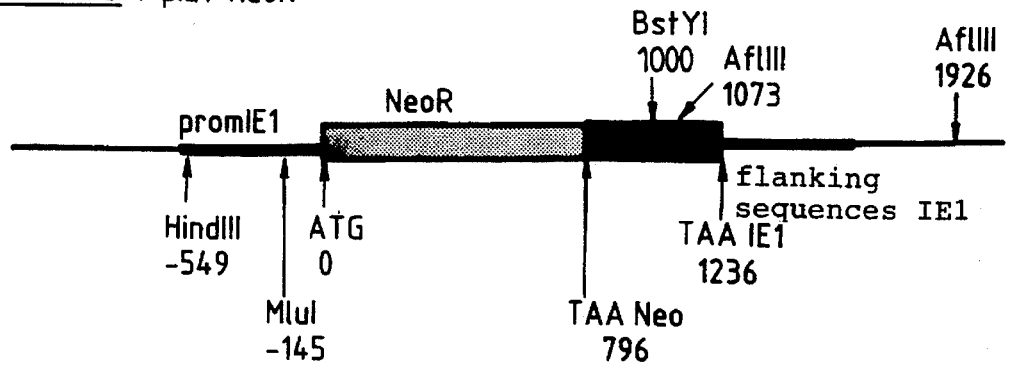

| WELLS | MW | 1 | 2 |
|---|---|---|---|
| | | |  |
| | 21226 — | | |
| | 7421 — | | |
| | 5804 — | | |
| | 4878 — | | |
| | 3530 — | | |

| WELLS | MW | 1 | 2 |
|---|---|---|---|
| | |  | |
| | 21226 — | | |
| | 5148 — | | |
| | 4266 — | | |
| | 3530 — | | |
| | 2027 — | | |
| | 1904 — | | |
| | 1584 — | | |
| | 1375 — | | |
| | 947 — | | |
| | 831 — | | |
| | 564 — | | |

FIGURE 4

```
                      ARS                         CDE I
AGACG)TTAGTCAAGTAATTCAAAAATATAATAGATTTAAGCATCACATGTTTGTAATCGGTA
 AccI                                             AflIII

ARS (C)
AAGTGAACCGAAGAGAGAGCACTACATTGCACAATAATTTGTTAAAATTGTTAGCTTTAA

CDE III
TATTACAGGGTCTGGTTCCGTTGTCCGACGCTATAACGTTTGCGGAACAAAAACTAAATT

ARS (MCCS)
GTAAATATAAAAAATTCGAACTTTAATTAATTATACATATATTTTGAATTTAATTAATTA

ARS
TACATATATTTTATATTATTTTTGTCTTTTATTATCGAGGGGCCGTTGTTGGTGTGGGGT

TTTGCATAGAAATAACAATGGGAGTTGGCGACGTTGCTGCGCCAACACCACCTCCTTCCT

ARS         ARS
CCTCCTTTCATCATGTATCTGTAGATAAAATAAAATATTAAACCTAAAAACAAGACCGCG

CCTATCAACAAAATGATAGGCATTAACTTGCGTGACGCTGTCACTAACGTTGGACGATTT

GCCGACTAAACCTTCATCGCCCAGTAACCAA(TCTAG
                                 XbaI
```

FIGURE 5

TC<u>CGATG</u>) TCTTTGTGATGCGCCGACATTTTTGTAGGTTATTGATAAAATGAACGGATACA
  ClaI

GTTGCCCGACATTATCATTAAATCCTTGGCGTAGAATTTGTCGGGTCCATTGTCCGTGTG

C<u>GCTAGC</u>ATGCCCGCTAACGGACCTCGTACTTTTGGCTTCAAAGGTTTTGCGCACAGACA
 NheI

AAATGTGCCACACTTGCAGCTCTGCATGTGTGCGCGTTACCACAAATCCCAACGGCGCAG

TGTACTTGTTGTATGCAAATAAATCTCGATAAAGGCGCGGCGCGC<u>GAATGC</u>AGCTGATCA
                                             BsmI

CGTACGCTCCTCGTGTTCCGTTCAAGGACGGTGTTATCGACCTCAGA<u>TTAATGTTTA</u>TCG

GCCGACTGTTTTCGTATCCGCTCACC(<u>AAAC</u>
                            MluI

FIGURE 7
Map of the PstI-N fragment of AcNPV
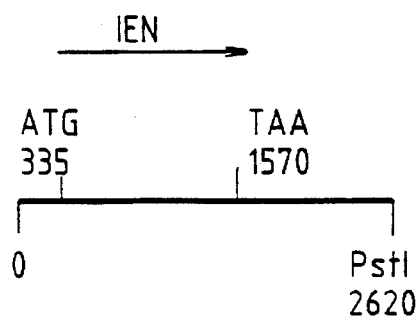
pIE1 NeoR IEN CAT
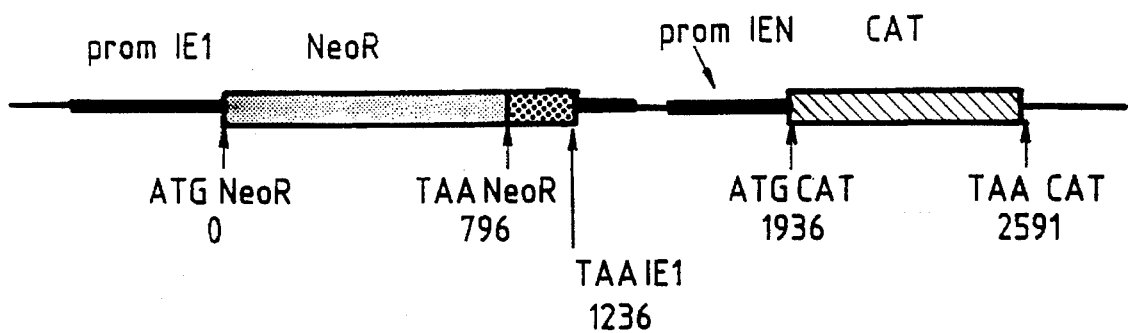

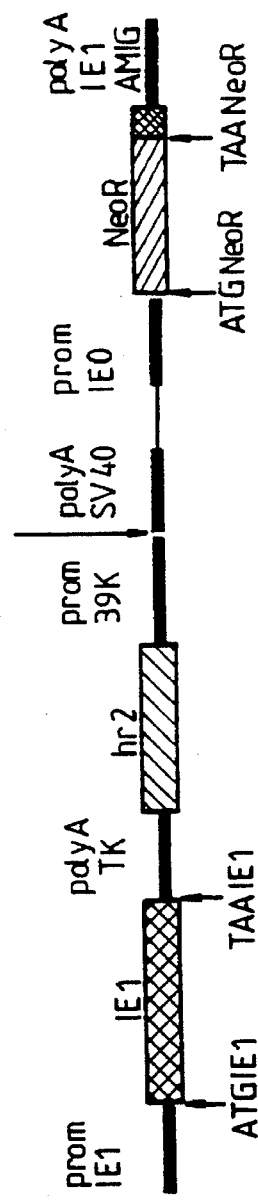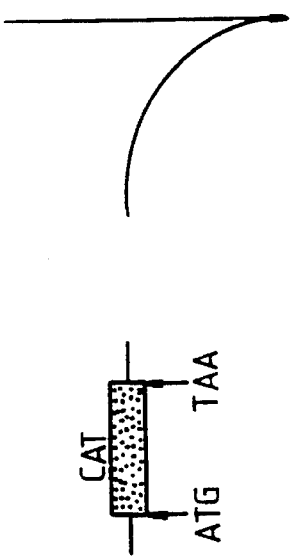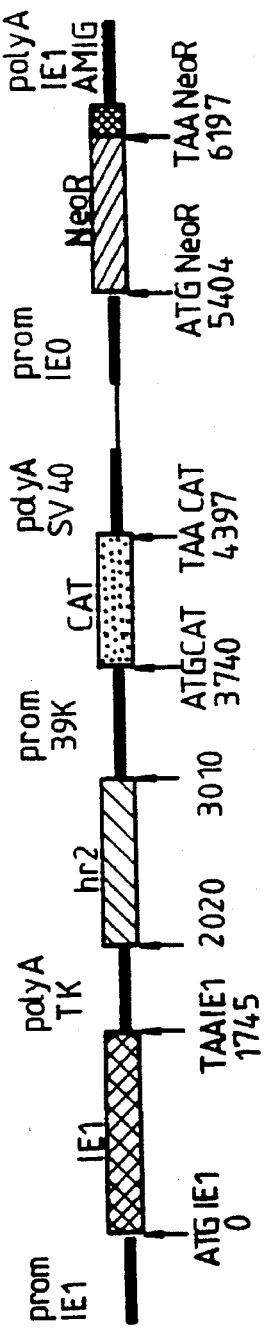
FIGURE 15a pC2 BglII
FIGURE 15b pC2 CAT

5,597,689

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 516 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Autographa californica nuclear polyhedrosis virus ( x i ) SEQUENCE DESCRIPTION: SEQ ID NO:1:

| | | | | | | |
|---|---|---|---|---|---|---|
| ACGTTAGTCA | AGTAATTCAA | AAATATAATA | GATTTAAGCA | TCACATGTTT | GTAATCGGTA | 60 |
| AAGTGAACCG | AAGAGAGAGC | ACTACATTGC | ACAATAATTT | GTTAAAATTG | TTAGCTTTAA | 120 |
| TATTACAGGG | TCTGGTTCCG | TTGTCCGACG | CTATAACGTT | TGCGGAACAA | AAACTAAATT | 180 |
| GTAAATATAA | AAAATTCGAA | CTTTAATTAA | TTATACATAT | ATTTTGAATT | TAATTAATTA | 240 |
| TACATATATT | TTATATTATT | TTTGTCTTTT | ATTATCGAGG | GGCCGTTGTT | GGTGTGGGGT | 300 |
| TTTGCATAGA | AATAACAATG | GGAGTTGGCG | ACGTTGCTGC | GCCAACACCA | CCTCCTTCCT | 360 |
| CCTCCTTTCA | TCATGTATCT | GTAGATAAAA | TAAATATTA | AACCTAAAAA | CAAGACCGCG | 420 |
| CCTATCAACA | AAATGATAGG | CATTAACTTG | CGTGACGCTG | TCACTAACGT | TGGACGATTT | 480 |
| GCCGACTAAA | CCTTCATCGC | CCAGTAACCA | ATCTAG | | | 516 |

( 2 ) INFORMATION FOR SEQ ID NO:2:

( i ) SEQUENCE CHARACTERISTICS:
( A ) LENGTH: 387 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Autographa californica nuclear polyhedrosis virus ( x i ) SEQUENCE DESCRIPTION: SEQ ID NO:2:

| | | | | | | |
|---|---|---|---|---|---|---|
| GATGTCTTTG | TGATGCGCCG | ACATTTTTGT | AGGTTATTGA | TAAAATGAAC | GGATACAGTT | 60 |
| GCCCGACATT | ATCATTAAAT | CCTTGGCGTA | GAATTTGTCG | GGTCCATTGT | CCGTGTGCGC | 120 |
| TAGCATGCCC | GCTAACGGAC | CTCGTACTTT | TGGCTTCAAA | GGTTTGCGC | ACAGACAAAA | 180 |
| TGTGCCACAC | TTGCAGCTCT | GCATGTGTGC | GCGTTACCAC | AAATCCCAAC | GGCGCAGTGT | 240 |
| ACTTGTTGTA | TGCAAATAAA | TCTCGATAAA | GGCGCGGCGC | GCGAATGCAG | CTGATCACGT | 300 |

```
ACGCTCCTCG TGTTCCGTTC AAGGACGGTG TTATCGACCT CAGATTAATG TTTATCGGCC        360

GACTGTTTTC GTATCCGCTC ACCAAAC                                            387
```

NUCLEOTIDE SEQUENCES PERMITTING THE REPLICATION AND MAINTENANCE OF A GENETIC INFORMATION IN ANIMAL CELLS

FIELD OF THE INVENTION

The present invention relates to vectors permitting the replication and maintenance of a genetic information in animal cells, in particular insect cells.

BACKGROUND OF THE INVENTION

The use of eukaryotic cells, and in particular animal cells, for the expression of cloned heterologous genes is the subject of numerous research studies. Indeed, only eukaryotic cells are capable of carrying out the post-translational modifications which are, in numerous cases, necessary for obtaining an active protein. At present, yeast constitutes one of the most widely used eukaryotic expression systems, because it is easy to use; however, the glycosylation system of yeasts, which differs somewhat from that of animal cells, does not permit certain proteins to be obtained in active form.

In order to obtain the expression of a gene in an animal cell, vectors of viral origin are used in particular. Among these, there may be mentioned baculoviruses which are currently used in numerous laboratories. Indeed, these viruses have the following advantages; they permit the insertion of long segments of DNA and possess, in addition, several strong promoters which are active at various stages of the virus replication cycle. These promoters are capable of inducing an extremely high level of expression of the genes placed under their control. Two late promoters, the polyhedrin promoter, and the protein P10 promoter, have been more particularly used for the expression of heterologous genes.

However, these baculovirus-derived expression vectors possess certain disadvantages which limit their use: first of all, the heterologous gene inserted into one of these vectors is expressed only within the framework of a viral infection; now, the viral infection results rapidly in the lysis of the cells, which means that the expression of a gene in the latter can only be transient, and which results, moreover, in the rapid degradation of the proteins produced by the cell. In addition, insofar as the heterologous gene is placed under the control of a late promoter, it is expressed only at the end of the virus replication cycle, at a stage when the cellular functions are already altered, and in particular the functions which bring about the post-translational modifications (for example the glycosylation).

Some teams have sought to solve these problems by inserting the heterologous gene whose expression is desired, no longer under the control of a late promoter, but of an early promoter. The genes placed under the control of early promoters are highly expressed from the beginning of the viral infection. Some of these promoters, for example the promoters of the IE1 [GUARINO and SUMMERS, J. Virol. 61:7, p. 2091–2099 (1987)], IE0, and IEN genes of the AcNPV baculovirus (Autographa californica nuclear polyhedrosis virus) are, contrary to the polyhedrin or P10 promoters, perfectly recognized by the cell RNA polymerase II. The expression of genes placed under the control of these promoters does not therefore depend on viral infection. It has thus been proposed to use the IE1 and IEN promoters to express, very early, heterologous genes.

It has also been proposed to use the sequence encoding protein IE1, in combination with a promoter of another baculovirus early gene, such as the 39K promoter (the protein encoded by the IE1 gene is a trans-activation factor for the expression of other baculovirus early genes, in particular of the 39K gene), and optionally with enhancer sequences (hr1, hr2, hr3, hr4, hr5) [GUARINO et al., J. Virol. 60:1, p. 224–229 (1986)] for the construction of expression vectors; (Application PCT/WO 92/05265 in the name THE TEXAS A & M UNIVERSITY SYSTEM designating as inventors GUARINO and JARVIS).

The aim pursued, in both cases, was to obtain, in particular, vectors which can be integrated into the cellular genome so as to stably express a heterologous gene under the control of a baculovirus early promoter. However, tee use of such vectors poses other problems. Indeed, neither the site nor the stability of integration into the cellular genome are controllable; now, these two parameters determine to a large extent the expression of the integrated gene.

Another approach to the problems posed by the expression of a heterologous protein in an animal cell consists in attempting to construct de novo an expression vector which, on the one hand, would replicate autonomously, and on the other hand would be maintained in the cell and be transmitted to its progeny. This means that this vector should contain at least one sequence ensuring the function of a replication origin which is active in the cell, as well as sequence ensuring its maintenance in the cell, and its segregation in the daughter cells during cell division.

Sequences active as extrachromosomal replication origin have been known for a long time in yeasts: these sequences, which are present in DNA portions, are called ARS (autonomously replicating sequences). The ARS elements possess two consensus sequences: one core sequence (A domain) which is necessary for the ARS function [KEARSEY, Cell., 37, 299–307, (1984)] but which, by itself, is not sufficient to permit the autonomous replication, and requires the presence of additional flanking sequences, and a 3' consensus sequence (C domain) situated downstream of the 3' end of the strand rich in T residues of the core sequence.

Although sequences similar to the consensus sequences of the ARS elements have been described in animal cells, their possible role in the replication of DNA in these cells has never been established. Several studies have been carried out with the aim of identifying sequences which are effectively active as replication origin in animal cells, in particular in mammalian cells [KRYSAN et al., Mol. Cell. Biol. 9, p. 1026–1033, (1989); HOLST et al., Cell 52, p. 355–365, (1988); cf also review by UMEK et al., Biochim. and Biophys. Acta, 1007, p. 1–14, (1989)]. However, in most cases, these studies have not resulted in the production of sequences permitting the replication and the maintenance of extrachromosomal genetic information.

In the case of insect cells, the only replication origin which has been identified is that of the *Drosophila melanogaster* mitochondrial DNA [SUGINO, Biochem. Biophys. Res. Commun. 91, p. 1321–1329, (1979)]. Although ARS sequences have also been localized in the genome of drosophila [GRAGEROV et al., Nucl. Acids Res. 16, p. 1169–1180, (1988)], their possible activity as replication origin has not been shown. As regards insect viruses, the presence, in at least 2 regions of the AcNMPV baculovirus genome, of sequences which behave like ARS elements when they are introduced into yeast cells, have been described [HOOFT VAN HIDDEKINGE et al., Arch. Virol. 88, p. 279–284, (1986)]. More recently, 4 fragments containing ARSs which are functional in *S. cerevisiae* have been identified [LEE et al., Virus Research, 24, p. 249–264, (1992)] in the genome of another baculovirus: the *Christoneura fumiferana* NPV baculovirus. Analysis of the sequence of the one among these fragments which has the highest ARS activity shows a region rich in A+T associated With a region of curved DNA. Although no sequence corresponds exactly to the core consensus sequence of the yeast ARS elements, 13 regions of sequences close to that of these elements (9 or 10 base pairs out of 11) have been identified. However, no indication is given on the functionality of these sequences in eukaryotic cells other than yeast cells. In particular, they are not presumed to be involved in the viral replication, all the more so since it has recently been shown [PEARSON et al., Science, 257, p. 1382–1384, (1992)] that in the AcNPV baculovirus, replication origins of the DNA are situated in the repetitive sequences, called hr sequences, of which each comprises several imperfect palindromes which are very similar to each other. These sequences, which are present in 6 regions distributed along the AcNPV genome, were previously known for their expression-enhancing properties [cf. publication by GUARINO et al. (1986), previously cited]. Deletion analysis of the hr sequences has made it possible to demonstrate that a sequence containing a single complete palindrome permitted the replication. Other authors [KOOL et al., Virology, 192, p. 94–101, (1993)] have described the detection and functional analysis of sequences present in the DNA of defective viruses, and which can serve as replication origin for AcNPV in the infected cells. The activity linked to the viral replication could be localized essentially in the 1,000 base pair region containing the highly repetitive DNA hr5.

SUMMARY OF THE INVENTION

With the aim of constructing stable vectors capable of autonomously replicating in Lepidoptera cells, the Inventors embarked, in a first stage, on the search for a replication origin which is active in the said cells.

For that, they constructed a plasmid (called hereinafter pIE1NeoR) containing a reporter gene for resistance to neomycin, inserted under the control of the promoter of the AcNPV baculovirus IE1 gene, with the intention of using, for the construction and screening of a genomic DNA library, *Spodoptera frugiperda* cells (Sf9) so as to search for cellular DNA sequences carrying a replication origin which is active in insect cells.

Now, during this work, the Inventors observed, surprisingly, that the plasmid pIE1NeoR was capable, in the absence of any DNA insert of cellular origin, of autonomously replicating in the cells, and that, in addition, this replication was accompanied, at the end of a few passages in culture, by an enhancement and a structuring of the plasmid genetic material in the form of an extrachromosomal structure of high molecular weight in the progeny of the cells initially transformed.

The Inventors have searched for the regions of the plasmid which were responsible for these properties, and have discovered that they were associated with the presence of a DNA sequence overlapping the portion of the IE1 gene encoding the COOH-terminal end of the IE1 protein as well as the flanking 3' region of this gene. This sequence, which will also be called in the following text "AMIG sequence" (Enhancement and Maintenance of Genetic Information), is indicated in the sequence listing in the annex under the number SEQ ID NO:1.

By carrying out the analysis of the AMIG sequence, with the aim of localizing the structures responsible for these properties, the Inventors identified several sequences related to the yeast ARS sequences, including one MCCS sequence of 11 bp homologous to the consensus sequence of the A domain of the ARS elements. They also localized sequences close to the consensus centromeric sequences of yeast and mammalian cells.

Moreover, the Inventors identified a sequence which is situated upstream of the promoter of the IE1 gene, and observed that this sequence acts to ensure the stability of the high-molecular weight extrachromosomal structure. This sequence, which will be called in the following text "STAB sequence" is indicated in the sequence listing in the annex under the number SEQ ID NO:2.

Various plasmids, comprising the AMIG and STAB sequences, in combination with various promoters have been constructed; all these plasmids possess the above-mentioned properties, namely that they are capable of replicating in transformed cells, and, in addition, of being maintained in their progeny, and of being structured in the form of very high-molecular weight episomes.

In the presentation of the present invention, "episome" is understood to mean an extrachromosomal and self-replicating DNA molecule.

The subject of the present invention is the use of a DNA fragment comprising the sequence indicated in the sequence listing in the annex under the number SEQ ID. NO:1, for producing a vector capable of autonomously replicating in an animal cell and of being maintained in the progeny of the said cell in the form of an episome.

According to a preferred embodiment of the present invention, the DNA fragment of sequence SEQ ID NO:1 is used in combination with a DNA fragment comprising the sequence indicated in the sequence listing in the annex under the number SEQ ID NO:2.

The subject of the present invention is, in addition, a vector capable of multiplying in an animal cell and of being maintained in the progeny of the said cell, characterized in that it is in the form of an episome consisting of a concatemer of a unit vector, which unit vector comprises the sequence indicated in the sequence listing in the annex under the number SEQ ID NO:1.

According to a preferred embodiment of the present invention, the said unit vector comprises, in addition, the sequence indicated in the sequence listing in the annex under the number SEQ ID NO:2.

For the purposes of the present invention, "concatemer" is understood to mean a DNA molecule consisting of at least 2 copies of the genetic information carried by the unit vector. The "unit vector" may comprise, in particular, in addition to the sequence SEQ ID NO:1, and advantageously, the sequence SEQ ID NO:2, at least one DNA fragment of which it is desired to obtain the multiplication in an animal cell and the maintenance in the progeny of the said cell. This may be in particular DNA fragments carrying the genetic information necessary for the production of proteins, or constituting a selectable marker, and the like.

The subject of the present invention is also a process for producing animal cell lines capable of transmitting to their progeny an extrachromosomal genetic information of heterologous origin, which process is characterized in that it comprises a step during which the transfection of an animal cell with a DNA preparation comprising at least one unit vector carrying the said genetic information and comprising the sequence indicated in the sequence listing in the annex under the number SEQ ID NO:1, or with a DNA preparation comprising at least one episome consisting of a concatemer of the said unit vector, is carried out, and a step during which the multiplication of the said animal cell and the selection of the progeny of the said cell carrying at least one episome consisting of a concatemer of the said unit vector, is carried out.

According to a preferred embodiment of the said process in accordance with the invention, the unit vector comprises, in addition, the sequence indicated in the sequence listing in the annex under the number SEQ ID NO:2.

It is possible to prepare episomal vectors in accordance with the invention by extracting DNA from cells selected after the process described above.

To obtain a unit vector permitting the implementation of the processes for producing animal cell lines and episomal vectors in accordance with the invention, the ligation, into an appropriate host vector, of the sequence indicated in the sequence listing in the annex under the number SEQ ID NO:1, and advantageously, of the sequence indicated in the sequence listing in the annex under the number SEQ ID NO:2, as well as of any other DNA sequence whose multiplication in an animal cell and maintenance in the progeny of the said cell it is desired to obtain, is carried out. The methods permitting the production of this unit vector are conventional genetic engineering methods, using commonly used host vectors such as those described by SAMBROOK et al. [Molecular Cloning: A Laboratory Manual, Second edition; Cold Spring Harbor Laboratory Press (1989)].

The subject of the present invention also encompasses stable cell lines capable of expressing a genetic information of heterologous origin, which lines are characterized in that each cell of the said line contains at least one episomal vector in accordance with the invention.

According to a preferred embodiment of the present invention, the said cell lines are insect, in particular lepidoptera, cell lines.

The present invention makes it possible to obtain an expression system which stably ensures the expression of a genetic information of heterologous origin in animal cells. This system can be used in particular for the production of recombinant proteins because it makes it possible to obtain, continuously and while ensuring a high level of expression, the protein of interest, independently of the integration of the gene encoding the latter in the cellular genome, and therefore without the uncertainties linked to this integration.

BRIEF DESCRIPTION OF THE FIGURES

FIG. 2A is a map of the pIE1 plasmid.

FIG. 2B is a map of the pIE1NeoR plasmid,

FIG. 4 is a listing of the nucleotide sequence of AMIG SEQ ID NO:1.

FIG. 5 is a listing of the nucleotide sequence of STAB SEQ ID NO: 2.

FIG. 7 is a map of the plasmid pIE1NeoRIENCAT.

FIG. 15a is a detailed representation of the vector pc2BglII.

FIG. 15b is a detailed representation of the vector pC2CAT.

DETAILED DESCRIPTION OF THE INVENTION

The present invention will be understood more clearly with the aid of the additional description below, which refers to examples for producing and using vectors comprising the AMIG sequences.

It goes without saying, however, that these examples are given purely as illustration of the subject of the invention and do not constitute in any manner a limitation thereto.

The general molecular biology techniques to which reference is made in the examples below are those described by SAMBROOK et al. [Molecular Cloning: A Laboratory Manual, Second edition; Cold Spring Harbor Laboratory Press (1989)].

EXAMPLE 1

CONSTRUCTION OF A PLASMID COMPRISING THE AMIG AND STAB SEQUENCES; REPLICATION OF THE SAID PLASMID IN INSECT CELLS AND FORMATION OF VERY HIGH-MOLECULAR WEIGHT EPISOMAL STRUCTURES

Figure 1:
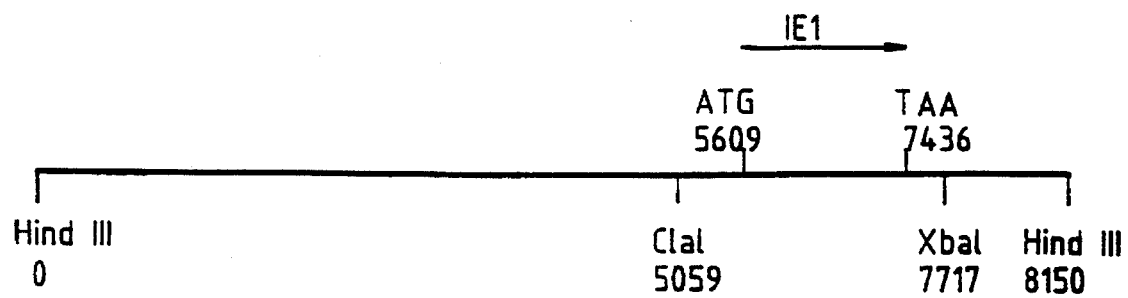
FIG. 1 is a map of the HindIII-G fragment of the AcNPV baculovirus.

The IE1 gene and its promoter are situated in the ClaI-XbaI subfragment (2658 bp) of the HindIII-G fragment of the AcNPV baculovirus (represented in FIG. 1). This ClaI-XbaI subfragment was excised, and then inserted into the plasmid pUC18, in place of the AccI-XbaI fragment of the latter: the plasmid pIE1 (represented in FIG. 2A) is thus obtained: (these bases are numbered from the A of the ATG codon of IE1).

The gene for resistance to neomycin (NeoR) was inserted into the plasmid pIE1 downstream of the promoter of the gene encoding the IE1 protein, in the following manner: the BglII-SmaI fragment of pNeo (PHARMACIA) was inserted in place of the HincII-AccI fragment of pIE1. The ends of the plasmid pIE1 and the BglII end of the fragment carrying the NeoR gene were, prior to the joining, rendered blunt by the action of Klenow polymerase. The plasmid thus obtained is called pIE1NeoR: the IE1NeoR insert is schematically represented in FIG. 2B: (these bases are numbered from the A of the ATG of NeoR.

The plasmid pIE1NeoR was used to transform *E. coli* DH5$_\alpha$ F'IQ (GIBCO-BRL), and purified on a CsCl gradient from recombinant bacteria selected on the basis of their resistance to ampicillin.

The plasmid pIE1NeoR was introduced by lipofection into the *Spodoptera frugiperda* cells (clone Sf9) according to the following procedure:

Two million cells are placed in a 25–cm$^2$ flask in TC100 medium (GIBCO) supplemented with 10% (v/v) of foetal calf serum. After one hour at room temperature, the cells became attached to the bottom of the flask. The medium is withdrawn and it is replaced with 3 ml of the said medium supplemented with 40 µl of DOTAP (BOEHRINGER)i and 10 µg of plasmid pIE1NeoR. After incubating for four hours at 28° C., the medium is again replaced with 4 ml of the same medium (TC100 +10% FCS), and comprising 1 mg/ml of G418 (GIBCO-BRL). After several passages in culture in this medium the cells are cloned in Petri dishes of 140 mm in diameter (about 100 cells/dish) in the same medium containing 3% methyl cellulose 3000–5000 (PROLABO) and 1 mg/ml of G418. The G418-resistant colonies are selected.

With the aim of characterizing the structure bearing the genetic information of pIE1NeoR, the total DNA of the G418-resistant cells was analysed by pulsed-field electrophoresis according to the following procedure: 2 million cells are harvested, washed twice with PBS and included in 1% agarose. After polymerization at 4° C., the agarose blocks are immersed in 5 volumes of lysis buffer (10 mM tris-HCl pH 8, 100 mM EDTA, 1% N-lauroylsarcosine, 200 µg/ml proteinase K) for 16 hours at 50° C. The blocks are then rinsed twice in TE buffer (10 mM tris-HCl pH 7.5; 1 mM EDTA) and then incubated for twice 2 hours at 37° C. in a PMSF solution (0.5 mM PMSF in TE) and again rinsed three times in TE. The blocks are then equilibrated for 16 h at 4° C., in the chosen restriction enzyme buffer, and then digested with 50 U of this enzyme overnight. The blocks thus prepared are directly loaded onto a 1% agarose gel (SEAKEM GTG), and the electrophoresis is carried out in 0.5× TBE running buffer (45 mM tris, 32 mM boric acid, 1.25 mM EDTA; pH 8.3).

The same analysis was carried out on the non-transformed control Sf9 cells.

Figure 3:
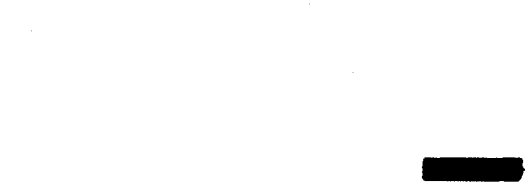
FIG. 3A is a Southern blot of non-transfected Sf9 cells (Lane 1) and Sf9 cells transfected with the plasmid pIE1NeoR (Lane 2).
FIG. 3B is a Southern blot of Sf9 cells transfected with the plasmid pIE1NeoR, undigested DNA (Lane 1) and Sf9 cells transfected with the plasmid pIENeoR, DNA digested with NcoI (Lane 2).
Figure 3:

FIG. 3 was established after the Southern transfers carried out pulsed-field electrophoresis gels of Sf9 DNA, after hybridization with a $^{32}$p probe ("pIE1NeoR probe") obtained by random priming on pIE1NeoR (BOEHRINGER MANNHEIM kit for labelling by random priming).

FIG. 3A: Digestion with BglII, running 18 hours, pulse 5 seconds, 200 V, 1% agarose gel in 0.5× TBE MW: molecular weight marker (expressed in bp);
Lane 1: non-transfected Sf9 cells (control);
Lane 2: Sf9 cells transfected with the plasmid pIE1NeoR;
FIG. 3B: running 4 h, pulse 5 s, 200 V, 1% agarose gel in TBE MW: molecular weight markers;
Lane 1: Sf9 cells transfected with the plasmid pIE1NeoR, undigested DNA
Lane 2: Sf9 cells transfected with the plasmid pIE1NeoR, DNA digested with NcoI.

A very high molecular weight form (about 300 kb) is detected in the undigested DNA or in the DNA digested by means of an endonuclease which does not have any cleavage site in the plasmid pIE1neoR, such as BglII. The molecular weight is higher in the case of the undigested DNA than in that of the DNA digested with BglII; this is explained by the fact that in the case of the undigested DNA, the running of the episomal structure is hampered by the chromosomal DNA of very high molecular weight.

When the DNA preparation is digested with a restriction endonuclease which has only one cleavage site in the plasmid sequence of pIE1NeoR, such as Nco*I*, a single fragment corresponding to the original size of plasmid pIE1neoR is observed.

The band showing a signal for hybridization with the probe pEI1neo (lane 2 of the gel B) was excised, and the DNA was extracted and prepared for observation under an electron microscope. Numerous circular DNA molecules were observed, and their length was estimated at about 112 µm, which corresponds to approximately 330 kbp.

These results indicate the presence, in the cells transformed with pIE1NeoR, of a large DNA structure in episomal form, consisting of concatemers of pIE1NeoR associated in direct tandem.

In addition, this structure can be extracted from the cells with a high efficiency by the alkaline lysis process [CARROL et al. Mol. Cell. Biol., 7, 1740–1750, (1987)], which is specific for circular structures regardless of their size. This extraction is carried out according to the following procedure: 5 million cells are taken up in 500 µl of lysis buffer (50 mM NaCl, 2 mM EDTA, 1% SDS, pH 12.45), vortexed for 2 min, incubated for 30 min at 30° C. Then 100 µl of 1M tris-HCl pH 7, 55 µl of 5M NaCl and 5 µl of proteinase K at 10 mg/ml are added. This mixture is incubated for 30 min at 37° C. After cooling, a phenol-chloroform extraction is carried out and the DNA is precipitated with ethanol.

The transfection of the Sf9 cells with 10 µg of the episomal form of pEI1neo (purified by the alkaline lysis method), makes it possible to obtain G418-resistant cells.

This very high-molecular weight episomal structure appears in the cells by multimerization of pIE1NeoR Over time. 25 days after transfection, pIE1NeoR is detected in the low-molecular weight DNA prepared from the G418-resistant cells, according to the procedure of HIRT [J. Mol. Biol. 26, 365–369, (1967)](which makes it possible to obtain DNA preparations enriched with low-molecular weight structures), and then separated on a 1% agarose gel, and appears under an electron microscope in the form of relaxed or supercoiled circular DNA molecules with an average length of 1.6 µm. This size corresponds to the theoretical size of the plasmid pIE1neoR. Moreover, it was observed that with the passages in culture, the signal corresponding to the plasmid pIE1NeoR (hybridization with the probe pIE1NeoR$^{32}$P) decreases in the DNA extracted by the HIRT method, whereas it increases in the total cellular DNA. In parallel, it was observed that the number of clones obtained by transforming *E. coli* with DNA extracted from cells by the HIRT method, decreases significantly with the time elapsed from the transfection: 200, 2 and 0 clones were obtained with the DNA extracted 25 days, 40 days and 70 days respectively after the transfection.

EXAMPLE 2:

CHARACTERIZATION OF THE DNA SEQUENCES RESPONSIBLE FOR THE PROPERTIES OF pIE1NeoR: LOCALIZATION OF THE AMIG AND STAB SEQUENCES

A series of plasmids were obtained by deleting fragments from pIE1NeoR:

pIE1NeoRΔA is obtained by deleting the fragment between the AflIII site situated at the end of the coding sequence in 3' of IE1 and the AflIII site of the vector pUC18;

pIE1NeoRΔN, pIE1NeoRΔB and pIE1NeoRΔM result from deletions in the flanking 5' region of the IE1 promoter:

pIE1NeoRΔN is obtained by deleting the fragment between the Nhe site of IE1 and the HindIII site of the multisite linker of pUC18;

pIE1NeoRΔB is obtained by deleting the fragment between the BsmI site of IE1 and the PstI site of the multisite linker of pUC18;

pIE1NeoRΔM is obtained by deleting the fragment between the MluI site of IE1 and the HindIII site of the multisite linker of pUC18.

After it has been checked that none of these deletions affected the function of the IE1 promoter, the deleted plasmids were used to transfect the Sf9 cells as described in Example 1.

All the plasmids permitted the production of a large number of resistant clones with the exception of the plasmid pIE1NeoRΔA which made it possible to obtain only a small number of G418-resistant clones.

Up to 100 days after the transfection, all the plasmids were still detected in the low-molecular weight DNA prepared from G418-resistant cells according to the HIRT procedure; however, the plasmid pIE1NeoRΔA is detected in a much smaller quantity than the other plasmids.

In the experiments carried out later (300 days after the transfection), the plasmids are no longer detected in the DNA extracted by the HIRT method.

The DNA from the G418-resistant Sf9 cells, obtained by extraction by alkaline lysis, comprises, for all the plasmids tested, with the exception of the plasmid pIE1NeoRΔA, high-molecular weight extra-chromosomal circular structures.

The neomycin-resistance observed in the cells transfected with the plasmid pIE1NeoRΔA therefore appears to result from the random integration of the plasmid pEI1NeoΔA in the cellular DNA.

When the total DNA prepared from transfected cells is digested with BglII numerous additional bands of lower intensity and of greater electrophoretic mobility are observed with the plasmids pIE1NeoRΔB, pIE1NeoRΔN or pIE1NeoRΔM, in addition to the major band corresponding to the episomal structure of high molecular weight. This observation suggests the presence of concatemers of plasmid integrated into the chromosome (these additional bands are not detected in the extracts obtained by alkaline lysis, which makes it possible to suppose that they are integrated forms).

Moreover, cells transfected with various plasmids have been subcloned and the clones obtained were analysed separately in order to see if the results observed reflected a homogeneous cellular behaviour, or the sum of the behaviour of cell subpopulations.

Clones obtained from cells transformed with pIE1neoR show the same behaviour as that of the total polyclonal cell population.

No labelled fragment was detected in the clones of cells transformed with pEI1neoΔA, which suggests that if the genetic information carried by the plasmid is present, it is only at a very low copy number.

The 3 clones derived from pEI1neoΔN have a behaviour identical to that of the polyclonal population, which suggests the presence, in the same cell, of episomal structures coexisting with plasmid copies which are integrated.

On the other hand, among the 4 clones derived from pIE1NeoRΔB, 2 have a behaviour similar to the clones derived from pIE1NeoRΔN and 2 have a behaviour similar to the clones derived from pIE1NeoRΔA. The same is true for the clones obtained from cells transformed with the plasmid pIE1NeoRΔM.

The experiments above made it possible to locate the portions of the plasmid pIE1NeoR responsible for its properties: the AccI-XbaI fragment from pIE1NeoR, which comprises the sequence identified in the sequence listing in the annex under the number SEQ ID NO:1 (AMIG sequence) carries the information essential for the plasmid replication; the ClaI-MluI fragment from pIE1NeoR, which comprises the sequence identified in the sequence listing in the annex under the number SEQ ID NO:2 (STAB sequence) carries an information which acts to favour the structuring of the plasmid in the form of an episome, and to stabilize the episomal structure.

The sequences SEQ ID NO:1 and SEQ ID NO:2 of the AMIG and STAB fragments were analysed: FIGS. 4 and 5 represent these sequences, where the regions representing specific characteristics are indicated:

the sequences of the restriction sites bordering the fragments are underlined, and are separated by brackets from the sequence of the rest of the fragments; the sequences of the restriction sites inside the fragments are underlined;

the sequences similar to the *S. cerevisae* CEN consensus sequences are in bold characters;

the sequences similar to yeast ARS consensus sequences are underlined with a double line.

The AMIG sequence (FIG. 4) has a segment (MCCS) which contains a complete homology with the 11 base pairs of the ARS elements, and 4 segments exhibiting a homology of 10 base pairs out of 11 with the core consensus sequence of the ARS elements and a segment which has a homology of 9 base pairs out of 11 with the ARS(C) consensus sequence situated upstream of the A domain in yeast ARS elements. All these sequences are comprised in a segment of 419 base pairs which contains abut 70% of A+T. Moreover, the AMIG sequence has a very large number of ATTA or ATTTA units and also has 2 sequences which are very similar to the consensus sequence of the binding site of the transcription factor NFI(nuclear factor I). Analysis of the AMIG sequence also reveals regions which are very similar to the *S. cerevisae* CEN consensus sequences. One of these sequences, M which is located from position 41 to position 471 (the numbering of the bases refers to that indicated in the sequence listing) exhibits 100% homology with the CDEI consensus sequence.

In addition, the sequences located from positions 77 to 263 and 158 to 166 are also very similar to the CDEII and CDEIII consensus sequences of yeast ARS elements. However, if the orientation of the CDEII/CDEIII block is compared with respect to CDEI in the plasmid pEI1neo and in yeast ARS elements, it is observed that these orientations are reversed.

The STAB sequence (FIG. 5) also has ATTA or ATTTA units, and sequences very similar to the consensus sequences of the binding sites of the transcription factors NFI (nuclear factor I) and NFIII, as well as an ARS-type sequence.

EXAMPLE 3:

CONSTRUCTION OF A PLASMID CARRYING THE AMIG SEQUENCE AND EXPRESSING THE NeoR GENE UNDER THE CONTROL OF THE IEO PROMOTER

The AcMNPV baculovirus IEO promoter was amplified by PCR in the form of a fragment flanked by KpnI and BssHII restriction sites. Its BsslIII end was repaired with Klenow polymerase, and it was then inserted in place of the KpnI-SmaI fragment of pUC19 giving the plasmid pIEO.

The BglII-BamHI fragment of pneo which contains the NeoR gene was then inserted into the BamIII site of pIEO so as to allow expression of the NeoR gene under the control of the IEO promoter, giving the plasmid pIEONeoR.

Figure 6:
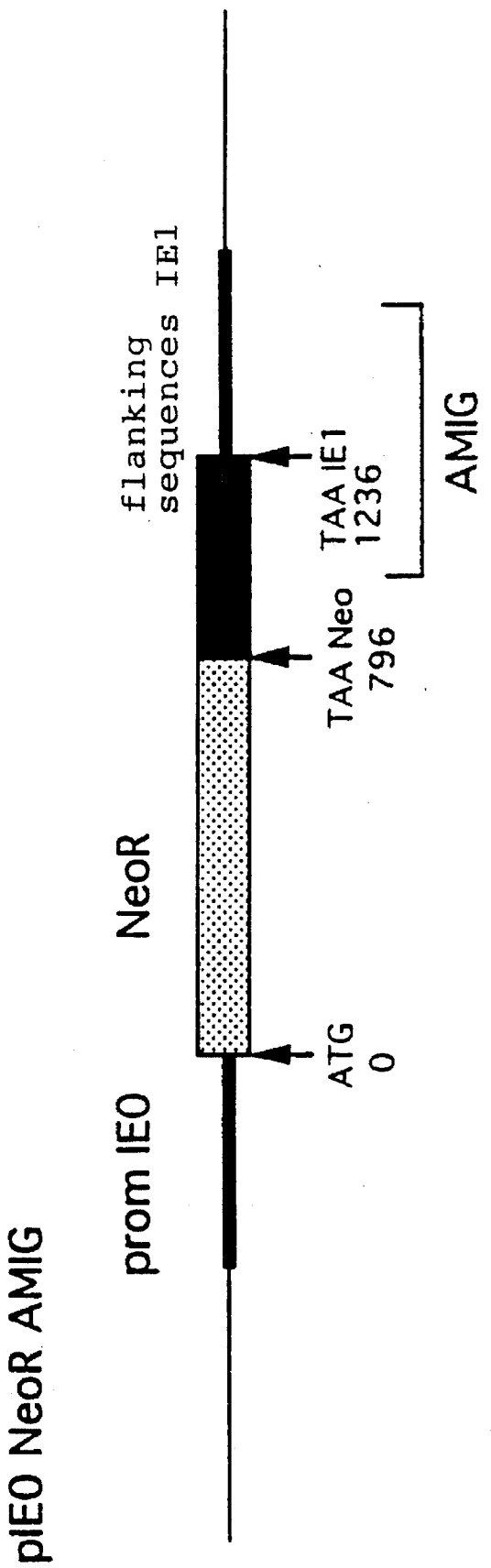
FIG. 6 is a map of the plasmid pIEONeoRAMIG.

The HincII-BamHI fragment of pIE1 which contains the AMIG sequence was inserted in place of the SmaI-BamHI fragment of pIEONeoR giving the plasmid pIEONeoRAMIG. This construct is represented in FIG. 6.

The Sf9 cells were transformed by lipofection with the construct pIEONeoRAMIG and the resistant cells selected With G418 at 1 mg/ml as described in Example 1.

After 10 passages, the DNA from these cells, extracted by alkaline lysis, was analysed by Southern transfer as described in Example 1. The genetic information is, in this case as well, present in the form of a high-molecular weight episome consisting of numerous tandem copies of the plasmid pIEONeoRAMIG.

EXAMPLE 4:

EXPRESSION, UNDER THE CONTROL OF A VIRAL PROMOTER, OF A GENE CARRIED BY A VECTOR COMPRISING THE AMIG AND STAB SEQUENCES IN THE PROGENY OF THE TRANSFORMED CELLS

A HindIII-XhoI fragment containing the IEN promoter from AcNPV was obtained according to the following procedure

- A XhoI linker of 8 bp was inserted into the BglII site of pNeo at −34 of the ATG of the NeoR gene. This gave the plasmid pNeoXhoI
- Plasmid pUC18IEN was constructed by inserting the PstI-N fragment of 2620 bp from AcNPV (which contains the IEN gene and its promoter) into the PstI site of pUC18. The BglII-PstI fragment of pUC18IEN containing the IEN promoter was subcloned into the plasmid pSelect (PROMEGA). One unique XhoI site was created in the ATG initiation codon of IEN by site-directed mutagenesis.

The HindIII-XhoI fragment of pUC18IEN containing the IEN promoter was inserted in place of the HindII-XhoI fragment of the plasmid pBLCAT2 (LUCKOW and SCHUTZ, Nucleic Acid Res., 15, (13) 5940 (1987)). The plasmid thus obtained is called pIENCAT.

The HindIII end of the HindIII-SacI fragment of pIEN-CAT comprising the IEN promoter and the CAT gene was repaired with Klenow polymerase and then the fragment was inserted between the SmaI and SacI sites of the plasmid pIE1NeoR to give the plasmid pIE1NeoRIENCAT. This construct is represented in FIG. 7.

The Sf9 cells were transformed (as described in Example 1) by lipofection with the construct pIE1NeoRIENCAT, and the resistant cells selected with G418 at 1 mg/ml.

After 10 passages, the cells were separated into 2 batches: one was maintained under a selection pressure and the other was not. After 15 additional passages, these two batches of cells were analysed by pulsed-field electrophoresis.

Figure 8:
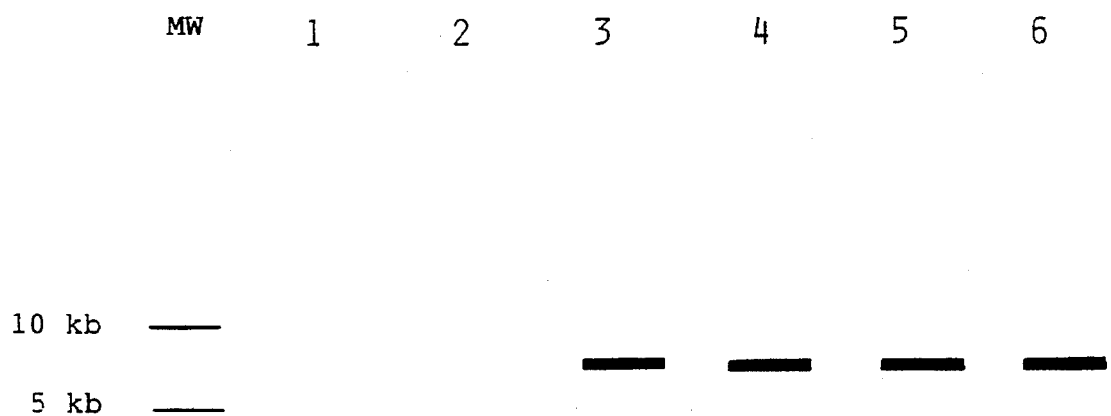
FIG. 8 is a depiction of pulsed-field electrophoresis results for: non-transformed Sf9 cells, BglII digestion (Lane 1); non-transformed Sf9 cells, HindIII digestion (Lane 2); Sf9 cells transformed with pIE1NeoRIENCAT, with selection pressure, BglII digestion (Lane 3); Sf9 cells transformed with pIE1NeoRIENCAT, with selection pressure, HindIII digestion (Lane 4); Sf9 cells tranformed with pIE1NeoRIENCAT, without selection pressure, BglII digestion (Lane 5); Sf9 cells tranformed with pIE1NeoRIENCAT, without selection pressure, HindIII digestion (Lane 6).

The results are represented in FIG. 8; the genetic information is still present in the form of a high-molecular weight episome consisting of numerous tandem copies of the plasmid pIE1NeoRIENCAT, and this whether the cells are maintained or not under a selection pressure. Furthermore, the copy number of the plasmid is comparable in both batches of cells.

Legend to FIG. 8:

MW: molecular weight marker (in bp)

Lane 1: non-transformed Sf9 cells, BglII digestion

Lane 2: non-transformed Sf9 cells, HindIII digestion

Lane 3: Sf9 cells transformed with pIE1NeoRIENCAT, selection pressure, BglII digestion (a single site in pIE1NeoRIENCAT);

Lane 4: Sf9 cells transformed with pIE1NeoRIENCAT, selection pressure, HindIII digestion (a single site in pIE1NeoRIENCAT);

Lane 5: Sf9 cells transformed with pIE1NeoRIENCAT, without selection pressure, BglII digestion;

Lane 6: Sf9 cells transformed with pIE1NeoRIENCAT, without selection pressure, HindIII digestion.

In addition, ELISA assay, on a total cell extract using an anti-CAT antibody (BOEHRINGER), of the CAT produced by the cells give identical results for both batches of cells as shown in Table I below.

These results show that the episomal structure is stable, including in the absence of selection pressure.

TABLE I

| | CAT concentration (ng/µg of cellular proteins) |
|---|---|
| 25 passages (+G418) | 0.25 |
| 10 passages (+G418) + 15 passages (−G418) | 0.26 |

EXAMPLE 5

EXPRESSION, UNDER THE CONTROL OF A CELLULAR PROMOTER, OF A GENE CARRIED BY A PLASMID VECTOR COMPRISING THE AMIG AND STAB SEQUENCES IN THE PROGENY OF THE TRANSFORMED CELLS.

The XhoI end of the XhoI-SacI fragment of the plasmid pCaSpcR-hs [THUMMEL and PIROTTA, Dros. inf. Sem. 71: 150 (1992)]was repaired with Klenow polymerase. This fragment contains the hsp70 promoter from *Drosophila melanogaster* and about 1000 bp of 3' sequences of this gene. These two elements are separated by a multiple cloning site containing, in particular, the BglII and StuI sites. This fragment was inserted in place of the SacI-SmaI fragment of pIE1NeoR to give the plasmid pIE1NeoRhsp.

Figure 9:
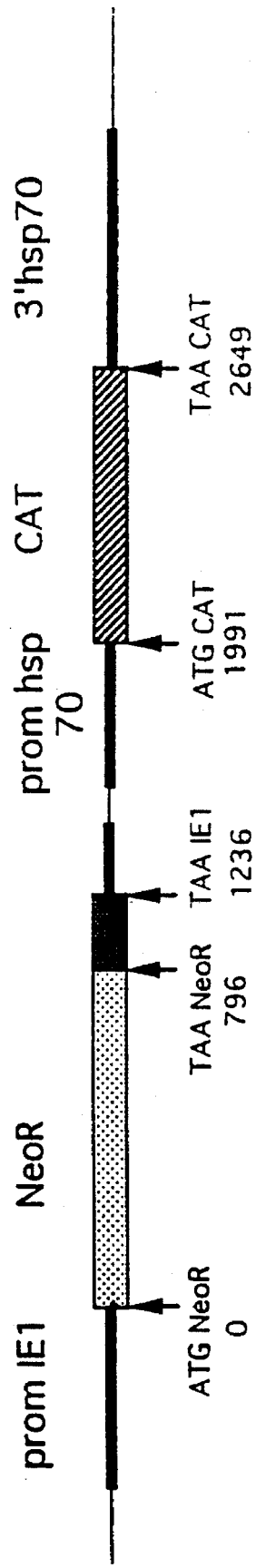
FIG. 9 is a map of the plasmid pIE1NeoRhspCAT.

The BglII-HindIII fragment of the plasmid pBLCAT2 which contains the CAT gene was inserted between the BglII and StuI sites of pIE1NeoRhsp to give the plasmid pIE1NeoRhspCAT. This construct is represented in FIG. 9.

The Sf9 cells were transformed by lipofection with the construct pIE1NeoRhspCAT and the resistant cells selected with G418 at 1 mg/ml as described in Example 1.

After 10 passages, the cells were separated into two batches: one maintained under a selection pressure and the other not. After 5 additional passages, the DNA from these two batches of cells was extracted by alkaline lysis and analysed by Southern transfer as described in Example 1. The genetic information is, in this case as well, present in the form of a high-molecular weight episome consisting of numerous tandem copies of the plasmid pIE1NeoRhspCAT.

In the Drosophila cells, the hsp70 promoter is inducible under the effect of a heat shock. The Sf9 cells transformed with pIE1NeoRhspCAT were therefore subjected to a heat shock of 0.5, 1 or 2 hours at 37° C. and the quantity of CAT produced was assayed by ELISA as described in Example 4.

Figure 10:
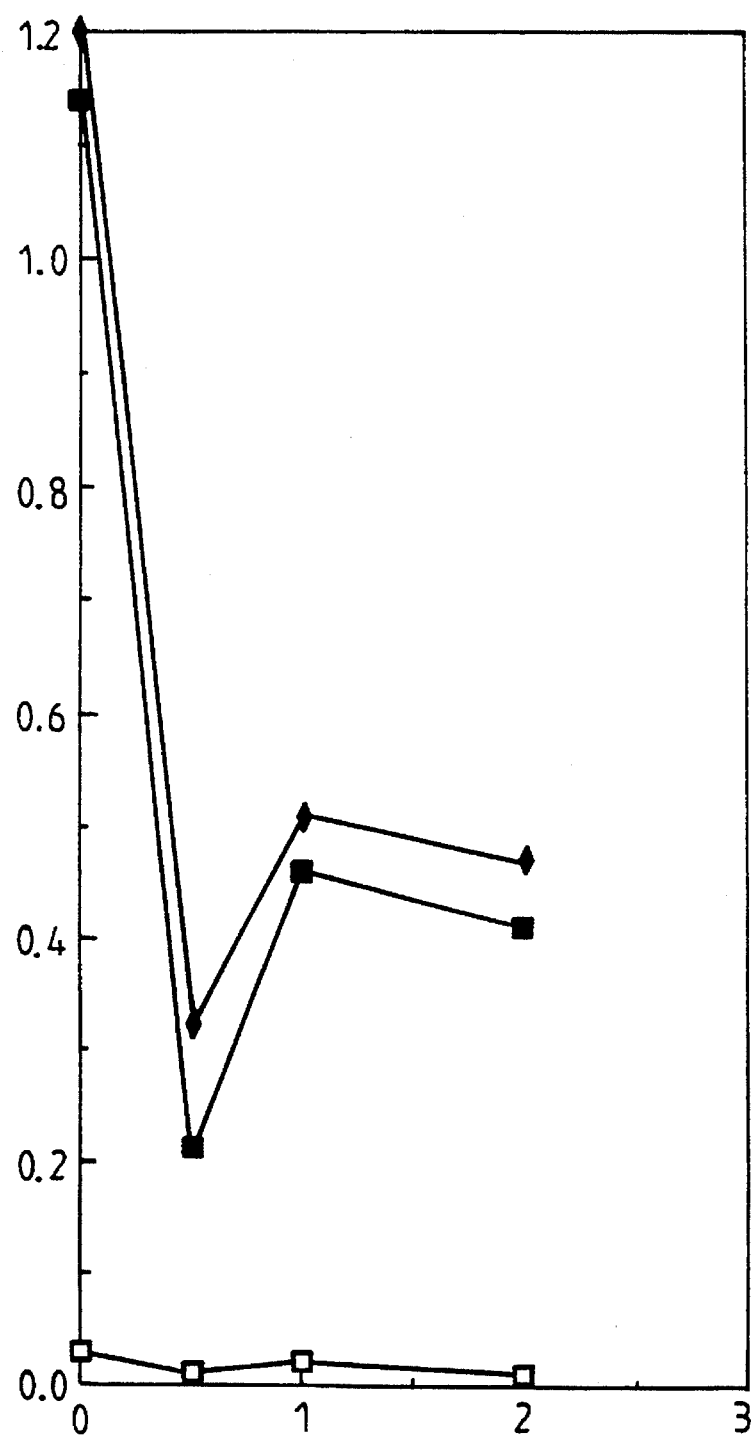
FIG. 10 is a graph plotting the quantity of CAT produced under ELISA as a function of time for three groups of Sf9 cells: nontransformed Sf9 cells; Sf9 cells transformed with pIE1NeoRhspCAT (10 passages without selection pressure); and Sf9 cells transformed with pIE1NeoRhspCAT (10 passages under selection pressure).

The results are presented in FIG. 10.

Legend to FIG. 10:

☐ Non-transformed Sf9 cells

♦ Sf9 cells transformed with pIE1NeoRhspCAT; 10 pas sages without selection pressure ■ SF9 cells transformed with pIE1NeoRhspCAT; 10 pas Sages under selection pressure The duration of the heat shock at 37° C. (in hours) is represented on the x-axis; the quantity of CAT produced (in ng/mg of total proteins) is represented on the y-axis.

These results show that:

The cells behave exactly in the same manner whether they are maintained under selection pressure or not.

The quantity of CAT produced under the control of the hsp10 promoter (1.2 ng/μg of total proteins) is much higher than under the control of the IEN promoter (0.25 ng/mg of total proteins: cf. Table 1, Example 4). However, the production is not inducible by heat shock; on the contrary, it decreases by a factor of 2 to 3.

EXAMPLE 6

EXPRESSION OF A GENE CARRIED BY A VECTOR COMPRISING THE AMIG AND STAB SEQUENCES, UNDER THE CONTROL OF A VIRAL PROMOTER TRANS-ACTIVATED AND CIS-ACTIVATED BY VIRAL ELEMENTS.

Figure 11A:
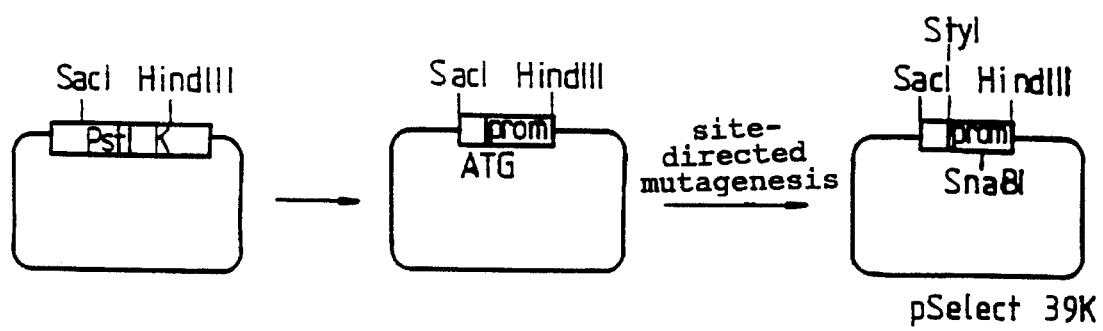
FIG. 11a is a flow chart illustrating the construction of the plasmid pSelect39K.

The 39K early promoter from the AcMNPV Baculovirus is trans-activated by the IE1 protein, the product of the IE1 gene [GUARINO and SUMMERS, Virol., 57: 563–571 (1986)]and cis-activated by the hr2 sequence [GUARINO and SUMMERS, Virol. 60: 215–223 (1986); and Virol. 60: 224–229, (1986)]. The inventors performed the stable expression of the CAT gene under the control of this promoter by making the following construction:

The PstI-K fragment from AcMNPV containing the 39K gene was inserted into the PstI site of pUC18. The SacI-HindIII fragment of the plasmid thus obtained contains the 39K promoter and the beginning of the coding sequence of the gone. It was inserted in place of the SacI-HindIII fragment of pSelect (PROMEGA). One unique StyI site was created in the ATG of 39K by site-directed mutagenesis, to give the plasmid pSelect39K. The steps of this construction are represented in FIG. 11a.

Moreover, the HindIII-L fragment from AcMNPV containing hr2 was inserted into the HindIII site of pUC18 giving the plasmid phr2.

Figure 11B:
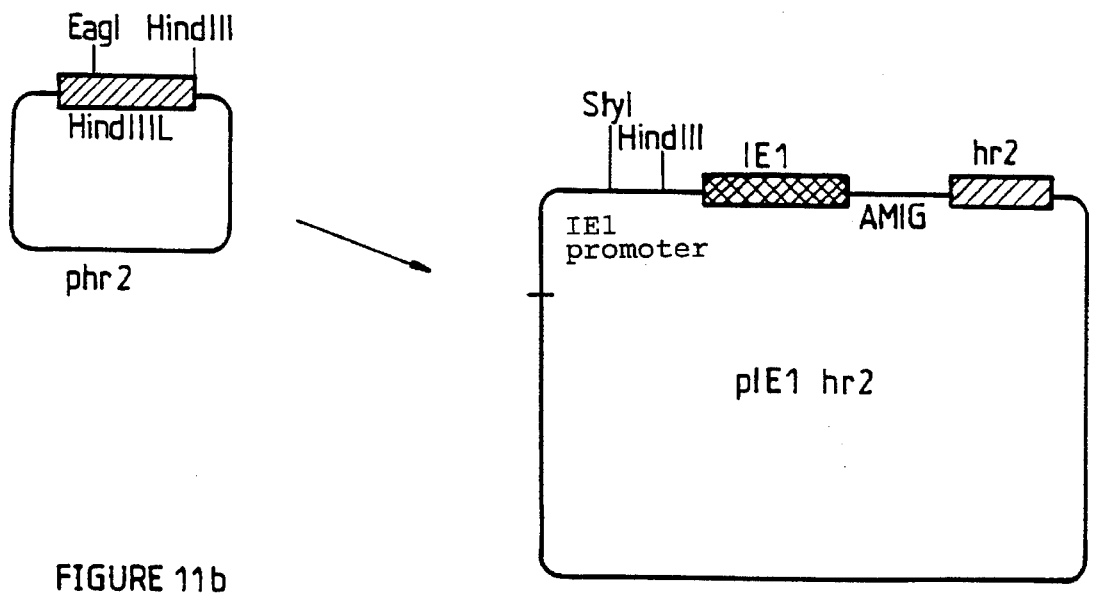
FIG. 11b is a flow chart illustrating the construction of the plasmid pIE1hr2.

The EagI-HindIII fragment of phr2 contains the entire hr2 sequences. Its ends were repaired with Klenow polymerase and this fragment was inserted into the XbaI site of pIE1 whose ends were also repaired with Klenow polymerase. The plasmid obtained is called pIE1hr2. The steps of this construction are represented in FIG. 11b.

The plasmid pIE1hr2 was digested with HindIII and StyI so as to remove the sites corresponding to these enzymes and reclosed after repairing the ends with Klenow polymerase.

The SnaBI-SacI fragment of pSelect39K containing the mutated 39K promoter, and a StyI site was inserted in place of the SnBI-SacI fragment of the plasmid pIE1hr2, giving the plasmid pIE1hr239K-1.

A BglII linker was inserted into the StyI site of pIE1hr239K-1.

The SacI-HpaI fragment of pBLCAT2 [LUCKOW and SCHULLZ, Nucl. Acids Res. 15:5490 (1987)]contains the polyadenylation sequences of the SV40 T antigen gene. It was inserted in place of the BspEI-SacI fragment of pIE1hr239K-1 after repairing the BspEI end with Klenow polymerase. The plasmid obtained is called pIE1hr239K-2.

To remove the BamHI site from pIE1hr239K-2, this plasmid was digested with BamHI and reclosed after repairing the ends with Klenow polymerase. A BamHI linker of 10 bp was then inserted into the SacI site of this plasmid, to give the plasmid pIE1hr239K-3.

Figure 12:
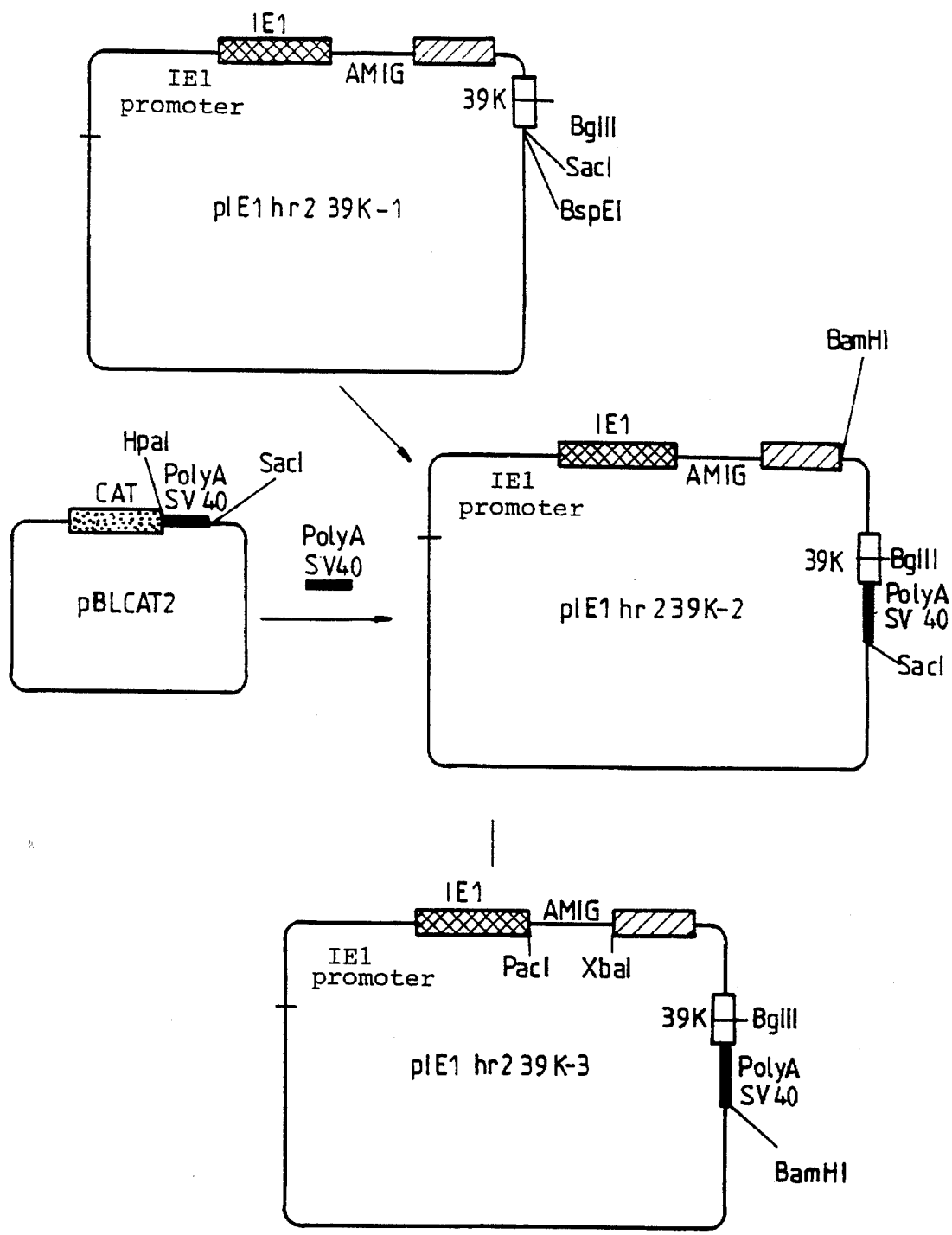
FIG. 12 is a flow chart illustrating the construction of the plasmids pIE1hr239K-1, pIE1hr239K-2, and PIE1hr239K-3.

The steps of the construction of pIE1hr239K-1, pIE1hr239K-2, pIE1hr239K-3 are schematically represented in FIG. 12.

The PacI-XbaI fragment of pIE1hr239K-3 contains the polyadenylation sequences of IE1 and the AMIG sequence. After repairing the Bsu36I and PacI ends with Klenow polymerase, it was replaced with the Bsu36I-AvrII fragment from pBKCMV (STRATAGENE) which contains the polyadenylation sequences of the CMV virus thymidine kinase gene. The plasmid obtained is called pIE1hr239K-4.

Figure 13:
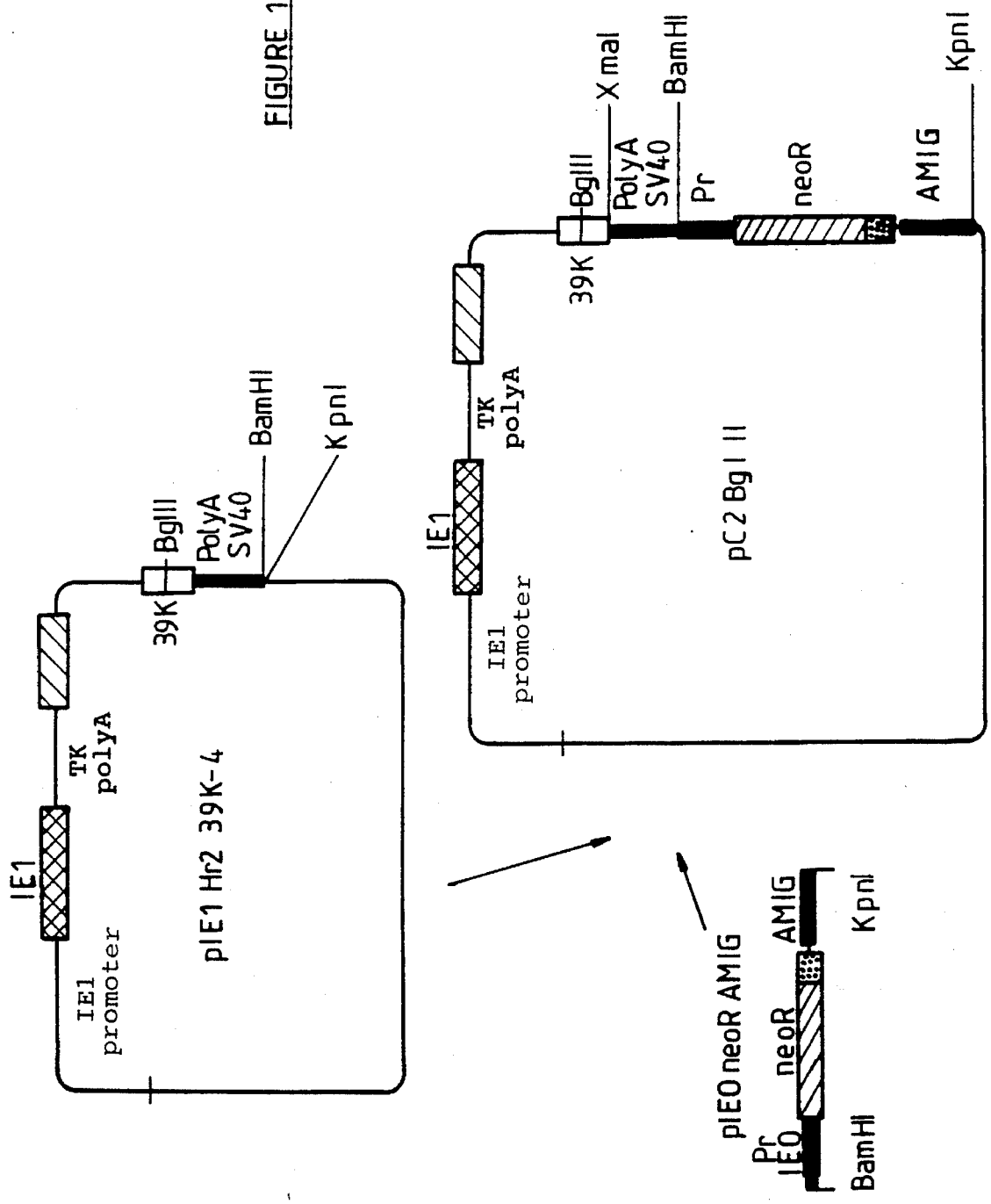
FIG. 13 is a flow chart illustrating the construction of the vector pc2 BglII.

The BamHI-KpnI fragment of pIEONeoRAMIG was inserted in place of the BamHI-KpnI fragment of pIE1hr239K-4, giving the expression plasmid pC2BglII in which a foreign gene can be inserted under the control of the 39K promoter in the unique BglII site. The steps of the construction of the vector pc2 BglII are represented in FIG. 13. A more detailed map of pC2BglII is represented in FIG. 15a.

The XmaI-BglII fragment of pBLCAT2 containing the CAT gene was inserted in place of the XmaI-BglII fragment of pC2BglII, giving the plasmid pC2CAT.

pC2CAT permits the expression of the genes:

NeoR under the control of the IEO promoter (polyA sequence: IE1)

IE1 under the control of the IE1 promoter (polyA sequence: CMV TK)

CAT under the control of the 39K promoter trans-activated by IE1 and cis-activated by hr2 (polyA sequence: SV40 T-Ag).

The STAB sequence is present upstream of IE1 and the AMIG sequence downstream of NeoR. Thus, they flank the coding sequences of the expression vector.

Sf9 cells were transformed by lipofection with the construct pC2CAT and the resistant cells selected with G418 at 1 mg/ml as described in Example 1.

After 10 passages, the DNA of these cells was extracted by alkaline lysis and analysed by Southern transfer. The genetic information is, in this case as well, present in the form of a high-molecular weight episome consisting of numerous tandem copies of the plasmid pC2CAT. The production of CAT, measured by ELISA assay, is 1.6 ng/mg of total proteins.

Figure 14:
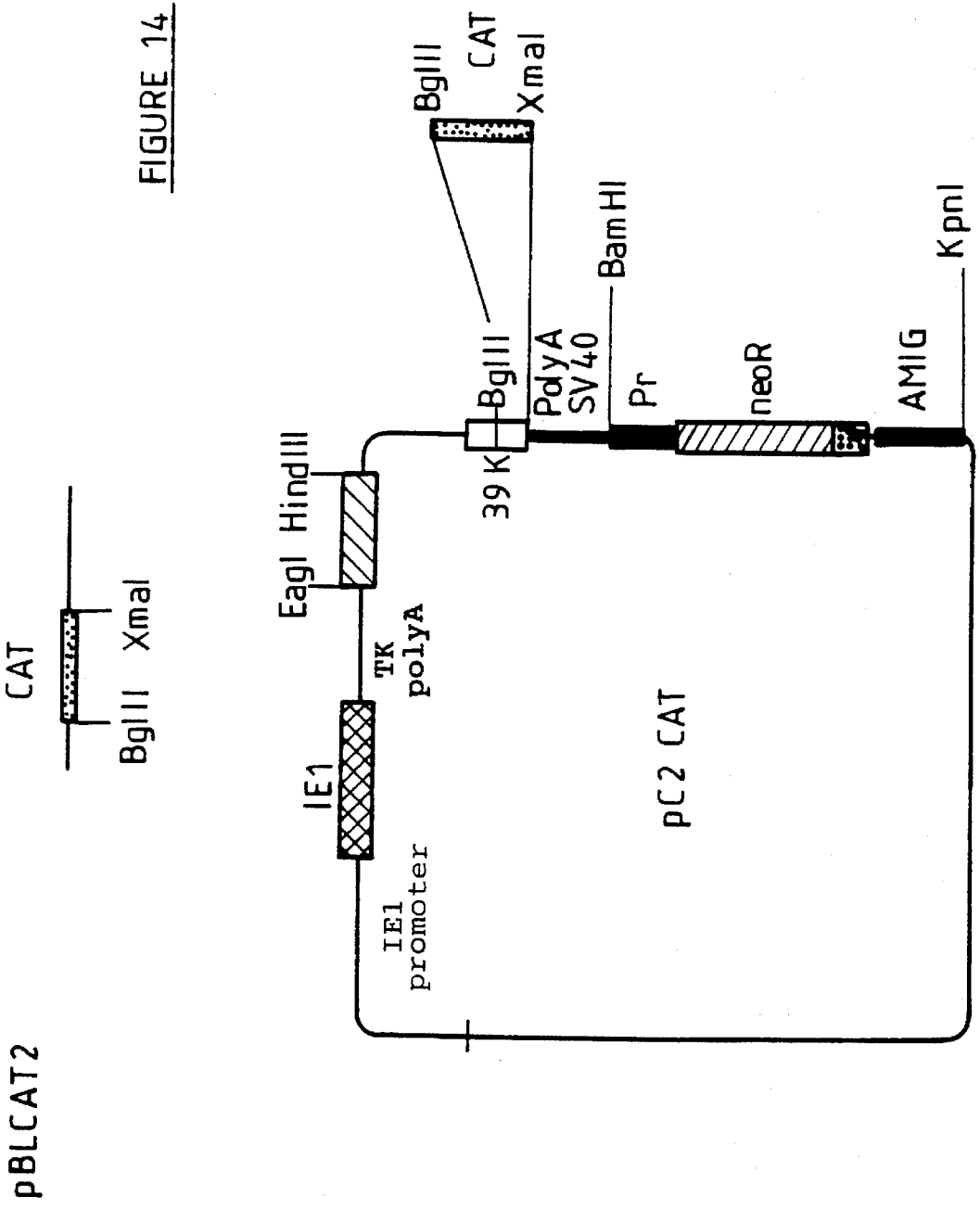
FIG. 14 is a representation of the vector pC2CAT.

The vector pC2CAT is represented in FIG. 14, and, in greater detail, in FIG. 15b.

We claim:

1. A process for producing a vector which autonomously replicates in a lepidopteran cell and is maintained in the progeny of the said cell in the form of an episome, said process comprising the step of ligating a DNA fragment consisting of the sequence SEQ ID NO:1 in a host vector.

2. A process according to claim 1, further comprising the step of ligating, into said vector, a DNA fragment consisting of the sequence SEQ ID NO:2.

3. A vector which can multiply in a lepidopteran cell and be maintained in the progeny of said cell, said vector being in the form of an episome consisting of a concatemer of a unit vector, said unit vector produced by the process of claim 1.

4. A process for producing a lepidopteran cell which transmits to its progeny extrachromosomal genetic information of heterologous origin, said process comprising the steps of:

a) providing at least one unit vector obtained by the process of claim 1 and carrying said genetic information of heterologous origin;

b) transfecting a lepidopteran cell with said unit vector;

c) culturing said cell so as to produce progeny thereof; and d) selecting among the progeny of said cell those cells carrying at least one episome consisting of a concatemer of said unit vector.

5. A stably transformed lepidopteran cell containing therein at least one episomal vector produced by the process of claim 1, said vector carrying genetic information of heterologous origin.

6. A vector which multiplies in a lepidopteran cell and is maintained in the progeny of said cell, said vector being in the form of an episome consisting of a concatemer of a unit vector, said unit vector being produced by the process of claim 2.

7. A process for producing a lepidopteran cell which transmits to its progeny extrachromosomal genetic information of heterologous origin, said process comprising the steps of:

a) providing at least one unit vector obtained by the process of claim 2 and carrying said genetic information of heterologous origin;

b) transfecting a lepidopteran cell with said unit vector;

c) culturing said cell so as to produce progeny thereof; and d) selecting among the progeny of said cell the cells carrying at least one episome consisting of a concatemer of said unit vector.

8. A stably transformed lepidopteran cell containing therein at least one episomal vector produced by the process of claim 2, said vector carrying genetic information of heterologous origin.

* * * * *

UNITED STATES PATENT AND TRADEMARK OFFICE
CERTIFICATE OF CORRECTION

PATENT NO. : 5,597,689
DATED : January 28, 1997
INVENTOR(S) : Devauchelle et al.

It is certified that error appears in the above-identified patent and that said Letters Patent is hereby corrected as shown below:

on the cover page, col. 1, OTHER PUBLICATIONS, "Pennoch" should be --Pinnock--;

on the cover page, col. 1, OTHER PUBLICATIONS, "Galactosides" should be --Galactosidase--;

col. 2, line 15, "tee" should be --the--;

col. 3, line 3, insert a space before "in";

col. 3, line 7, "With" should be --with--;

col. 3, line 16, insert a space before "that"

col. 3, line 27, insert a space before "have";

col. 4, line 53, omit "35";

col. 5, line 55, after "plasmid" the comma (,) should be a period (.);

col. 6, line 53 in the sub-heading, insert a colon (:) after "EXAMPLE 1";

col. 7, line 26, before "and" omit "i";

col. 7, line 61, after "out" insert --using--;

UNITED STATES PATENT AND TRADEMARK OFFICE
CERTIFICATE OF CORRECTION

PATENT NO. : 5,597,689
DATED : January 28, 1997
INVENTOR(S) : Devauchelle et al.

It is certified that error appears in the above-identified patent and that said Letters Patent is hereby corrected as shown below:

col. 7, line 63, "p" should be --P--;

col. 8, line 52, "Over" should be --over--;

col. 10, line 61, omit "M";

col. 10, line 62, "471" should be --47--;

col. 10, line 65, "77" should be --177--;

col. 11, line 31 "With" should be --with--;

col. 11, line 60 "Hind II" should be --Hind III--;

col. 12, line 48, in the sub-heading, insert a colon (:) after "EXAMPLE 5"

col. 12, line 57, insert a space before "was";

col. 13, line 24, "pas Sages" should be --passages--;

col. 13, line 48, insert a space before "and";

col. 13, line 57 "gone" should be --gene--;

col. 14, line 14, insert a space before "contains".

Signed and Sealed this

Twentieth Day of May, 1997

BRUCE LEHMAN

*Attest:*

*Attesting Officer*

*Commissioner of Patents and Trademarks*